US008946115B2

(12) United States Patent
Pianzola et al.

(10) Patent No.: US 8,946,115 B2
(45) Date of Patent: Feb. 3, 2015

(54) CATALYSTS FOR THE PREPARATION OF METHYLPYRIDINE

(71) Applicants: Daniel Pianzola, Glis (CH); Walter Siegrist, Visp (CH)

(72) Inventors: Daniel Pianzola, Glis (CH); Walter Siegrist, Visp (CH)

(73) Assignee: Lonza Ltd, Basel (CH)

( * ) Notice: Subject to any disclaimer, the term of this patent is extended or adjusted under 35 U.S.C. 154(b) by 0 days.

(21) Appl. No.: 14/013,796

(22) Filed: Aug. 29, 2013

(65) Prior Publication Data

US 2014/0051569 A1 Feb. 20, 2014

Related U.S. Application Data

(62) Division of application No. 12/903,550, filed on Oct. 13, 2010, now Pat. No. 8,530,664.

(60) Provisional application No. 61/252,336, filed on Oct. 16, 2009.

(51) Int. Cl.
*B01J 23/44* (2006.01)
*C07D 213/16* (2006.01)
*B01J 21/08* (2006.01)
*B01J 21/12* (2006.01)
*B01J 37/18* (2006.01)

(52) U.S. Cl.
CPC ............... *B01J 23/44* (2013.01); *C07D 213/16* (2013.01); *B01J 21/08* (2013.01); *B01J 21/12* (2013.01); *B01J 37/18* (2013.01)
USPC .......................................... 502/262; 546/252

(58) Field of Classification Search
CPC ........ C07D 213/16; B01J 21/08; B01J 21/12; B01J 23/44; B01J 3/187
USPC ........................................ 502/262; 546/252
See application file for complete search history.

(56) References Cited

U.S. PATENT DOCUMENTS

| 5,714,610 | A | * | 2/1998 | Heveling et al. | ............... | 546/184 |
| 5,847,131 | A | * | 12/1998 | Simon et al. | .................. | 544/178 |
| 6,118,003 | A | * | 9/2000 | McAteer et al. | ............... | 546/286 |
| 8,637,668 | B2 | * | 1/2014 | Wigbers et al. | ............... | 544/178 |

OTHER PUBLICATIONS

Klinkenberg "Aromatic formation in . . . " p. 1-91 (1957).*

* cited by examiner

*Primary Examiner* — Celia Chang
(74) *Attorney, Agent, or Firm* — Hoffmann & Baron, LLP

(57) ABSTRACT

Subject of the invention is a dehydrogenation catalyst for dehydrogenating methylpiperidine to methylpyridine. Subject of the invention are also methods for preparing the catalysts obtained thereby and methods, in which the catalysts are used.

5 Claims, No Drawings

CATALYSTS FOR THE PREPARATION OF METHYLPYRIDINE

CROSS-REFERENCE TO RELATED APPLICATION

The present application is a divisional application of U.S. Ser. No. 12/903,550, which claims priority to U.S. Provisional application 61/252,336, the contents of both applications are herein incorporated by reference.

This application claims the benefit of priority from U.S. Provisional Patent Application No. 61/252,336 filed Oct. 16, 2009, the disclosure of which is incorporated herein by reference.

Subject of the invention is a dehydrogenation catalyst for dehydrogenating methylpiperidine to methylpyridine. Subject of the invention are also methods for preparing the catalysts and methods, in which the catalysts are used.

BACKGROUND OF THE INVENTION 3-methylpiperidine and 3-methylpyridine (3-picoline) are intermediates in the industrial production of nicotinic amide and nicotinic acid, which is an essential vitamin of the B-complex (vitamin $B_3$). In this process, 3-methylpiperidine is converted to 3-methylpyridine in the presence of a dehydrogenation catalyst. The 3-methylpyridine is converted to 3-cyanopyridine by oxidative ammonolysis. The 3-methylpiperidine can be obtained by cyclization of 2-methyl-1,5-diaminopentane.

Catalysts function to increase the rate of a chemical reaction at a given temperature by lowering the necessary amount of energy to reach the transition state. They can be present in the same phase as the reaction educts (homogenous catalysts) or in a different phase (heterogeneous catalysts).

Methylpyridines are also used as organic solvents. Further, they are used in organic synthesis for producing derivatized products thereof. 3-picoline is a colourless, combustible liquid which is also used in the production of pharmaceuticals, dyes, rubber chemicals, resins and insecticides.

EP 0 770 687 B1 discloses the industrial synthesis of nicotinic acid amides, starting from 2-methyl-1,5-diaminopentane. This compound is converted to 3-methylpiperidine in the presence of a catalyst comprising an oxide of aluminium and/or silicon.

Subsequently, the 3-methylpiperidine is passed over a dehydrogenation catalyst and converted to 3-picoline. The 3-picoline is converted to 3-cyanopyridine with a further catalyst. Finally, the nicotinic acid amide is obtained in an enzymatic reaction.

In the art, various catalysts are known for dehydrogenating cyclic alkanes to arylic compounds. For instance, U.S. Pat. No. 4,401,819 discloses the use of palladium deposited on silica, alumina or carbon for the preparation of pyridine and substituted pyridines from piperidine and related compounds.

A method for preparing 3-methylpyridine from 3-methylpiperidine with a dehydrogenation catalyst is also disclosed in CN 1903842 A. In this process, the catalyst is based on palladium coated on a silicon dioxide carrier.

Specific catalysts for converting 3-methylpiperidine to 3-methylpyridine are also disclosed in WO 94/22824. The catalysts consist of palladium or platinum as the active component coated on a carrier comprising oxides of aluminium and/or silicon. In a specific embodiment, the dehydrogenation catalysts are obtained by impregnating silicon-aluminium oxide with a solution of a palladium-ammonia complex.

Thus, there is a continuing need for efficient processes for producing methylpyridines and for efficient catalysts, which are readily available. Specifically, there is a need for efficient catalysts which allow conversion of methylpiperidine to methylpyridine with a high yield. Further, there is a need for catalysts and processes, which keep the amount of undesired side-products low.

Another problem of palladium-based catalysts is that they can easily be inactivated by oxygen or other process chemicals (catalyst poisoning). Therefore, when such catalysts are used in an industrial process, their lifetime is limited. There is thus a need for catalysts, which are stable against inactivation and can be used in an industrial process for an extended time. Further, there is a need for processes for the production of methylpyridine, in which the conditions are adjusted such that catalysts can be used for a long time. The increase of catalyst lifetime is significant for reducing the costs of such a process, because palladium is an expensive precious metal. Further, the interruption times of the industrial continuous production process can be reduced when the catalyst is reactive over a long time period. Thus, costs can be kept low and product uniformity is preserved.

DISCLOSURE OF THE INVENTION

Subject of the invention is a process for the production of a catalyst for the dehydrogenation of methylpiperidine to methylpyridine, comprising in the order (a) to (d) the steps of
(a) providing a carrier comprising 65-100 weight % silicon oxide and 0-35 weight % aluminium oxide,
(b) impregnating the carrier with palladium, whereby the carrier is brought into contact with an aqueous solution of a palladium-ammonia-complex to obtain a catalyst,
(c) drying the catalyst at a temperature below 80° C. and
(d) calcinating the catalyst at a temperature below 200° C.

In a specific embodiment of the invention, the steps (a) to (d) are carried out in one single reactor.

In a preferred embodiment of the invention, the drying step (c) is carried out with air and/or at a temperature between 20° C. and 60° C., preferably between 25° C. and 50° C. or between 30° C. and 45° C. In a preferred embodiment, the drying step is carried out at 40° C. Preferably, the drying step is carried out under air. The drying step is finished when essentially all the water is removed from the catalyst. In an embodiment of the invention, the drying step is carried out for 5 hours to 7 days, preferably for 1 to 5 days.

In a preferred embodiment of the invention, the calcinating step (d) is carried out under air and/or at a temperature between 80° C. and 200° C., preferably between 100° C. and 180° C., more preferably between 100° C. and 160° C., even more preferably between 120 and 140° C. In a preferred embodiment, the calcinating step is carried out at 130 or 140° C. The calcinating step may be carried out for a time range between 2 and 72 hours, more preferably between 6 and 36 hours. In a preferred embodiment, the calcinating step (d) is carried out for 8 h at 140° C. In general, if the temperature of the calcination step is set relatively high, a lower treatment time is necessary and vice verse.

In the drying step (c) water is removed from the catalyst. In this step, essentially water is removed which is not crystal water, but merely wettening the catalyst due to the aqueous production process. In the calcinating step (d) the crystal structure of the catalyst is amended. In this step, crystal water may be removed from the catalyst. Of course, also residual non-crystal water may be removed in this step. Surprisingly, it was found that a highly efficient catalyst can be obtained when carrying out a drying step (c) and a calcinating step (d)

at relatively low temperatures as outlined above. It was found that when calcinating the catalyst at higher temperatures, the efficiency of the catalyst is strongly decreased. Further, it was found that when including a drying step at a low temperature as outlined above, the efficiency of the catalyst is significantly increased. Altogether, these findings were surprising because in the art drying and calcinating were usually combined in one step, or a calcinating step was applied at a significantly higher temperature. For instance, CN 1903842 discloses calcination of a catalyst at 650° C., combined with drying at 110° C. to 120° C.

In a preferred embodiment of the invention, after the drying step (d) the catalyst is activated in a step (e) with hydrogen. It was found that the catalytic activity of the catalyst of the invention is significantly enhanced upon activation. It is not necessary to activate the catalyst directly after drying and calcinating. In contrast, the catalyst obtained after the calcinating step (d) was found to be relatively stable after calcinating and may be stored or transported. Preferably, the activation of the catalyst (e) is carried out immediately before using the catalyst in the dehydrogenation process. Preferably, the time between activation and use of the catalyst is shorter than one hour, preferably less than 10 or 30 minutes. After activation, the catalyst was found to be labile. Preferably, it should be continuously be subjected to a hydrogen stream between activation and use. In an embodiment of the invention, the activation (e) is carried out in the same reactor in which the subsequent dehydrogenation reaction is carried out.

The activating step (e) is carried out under a hydrogen stream. In a further embodiment of the invention, the activating step (e) is carried out under hydrogen and nitrogen. For instance, the mixture may comprise 20 to 80% hydrogen and 20 to 80% nitrogen, preferably 50% hydrogen and 50% nitrogen (volume/volume). In a preferred embodiment, the activating step is carried out at least in part at an elevated temperature. It is preferred that after the calcination step, the catalyst is cooled or allowed to cool, preferably to room temperature or to a temperature below 40° C. The initial activation with hydrogen may start at this temperature. For instance, the activation temperature may be between 25° C. and 450° C. In a preferred embodiment, the temperature is increased during the activating process, for example up 350° C. or up to 300° C. Whilst increasing the temperature, an amount of hydrogen may be added which is adapted to the rising temperature. In a preferred embodiment, the temperature is increased until the reaction temperature of the subsequent dehydrogenation reaction is reached. In a preferred embodiment, the temperature is increased to between 250 and 320° C., preferably to about 290° C., and the subsequent reaction is carried out at that temperature.

The activating step (e) is carried out under exclusion of oxygen. In a preferred embodiment of the invention, the activating step (e) is carried out under active depletion of oxygen. It was found that the catalyst is more efficient when oxygen is strictly excluded from the reactor during treatment with hydrogen. In a preferred embodiment, a deoxygenation catalyst is used for actively depleting the hydrogen stream and/or the reaction vessel of oxygen. It was found that oxygen depletion can be significantly supported by a catalyst, which converts oxygen and hydrogen to water. The deoxygenation catalyst may comprise palladium. The palladium may be coated on a support, such as alumina. In a specific embodiment, a conventional exhaust gas catalytic converter is used. A preferred deoxygenation catalyst is available under the trademark PuriStar R0-25 S6 from BASF AG In a preferred embodiment of the invention, the deoxygenation catalyst is provided in a double shell pipe.

In step (b), the carrier is impregnated with an aqueous solution of a palladium-ammonia complex. Preferably, the solution is obtained by preparing a solution of palladium chloride and dissolving ammonia in the solution. Preferably, the impregnation of the carrier is carried out for 6 hours to 72 hours, preferably for about 24 hours. During the impregnation step, the carrier is preferably stirred. Alternatively, the carrier is arranged as a fixed bed and impregnation solution flows through it.

The carrier used in step (a) comprises silicon oxide and optionally aluminium oxide. In a specific embodiment, the catalyst consists of silicon oxide. In a preferred embodiment, the catalyst essentially consists of 65 to 100 weight % silicon oxide and 0 to 35 weight % aluminium oxide. The catalyst might comprise below 5 weight %, 1 weight %, or 0.5 weight % of other components, for instance due to impurities. Preferably, the silicon oxide is SiO2 and the aluminium oxide is $Al_2O_3$. For instance, the catalyst is obtainable by preparing a mixed oxide of $Al_2O_3$ and $SiO_2$. Preferably, the catalyst is prepared in a sol/gel process. Such carrier materials are known in the art and commercially available. A useful carrier based on silicon oxide and aluminium oxide is Grace Davicat E501™ from Grace Inc. However, the catalyst may also have a special crystallized structure, such as an aluminium silicate or a zeolite. Preferably, the specific surface area of the catalyst is at least 50 $m^2/g$, more preferably at least 100 $m^2/g$. The specific surface area may be in the range of 100 to 700 $m^2/g$, or between 200 to 500 $m^2/g$, and is preferably about 300 $m^2/g$.

The carrier is provided in the form of a granulate. The average diameter of the granules may be between 0.05 and 10 mm, preferably between 0.1 and 5 mm or between 0.5 and 2 mm. In a preferred embodiment, short strands of the carrier are used, for instance the strands may have a diameter between 0.2 and 3 mm, or between 0.5 and 1.5 mm, and a length of 2 to 10 mm, preferably 4 to 8 mm. Prior to the treatment with the palladium-ammonia complex, the carrier may be dehydrated. The carrier is a Lewis acid by nature. Therefore, in the inventive process the carrier is preferably neutralized with ammonia before the impregnating step (b). When a non-porous carrier is used, the palladium is attached to the surface of the carrier. In a preferred embodiment of the invention, the catalyst comprises 0.5 to 8 weight %, preferably 1 to 6 or 2 to 5 weight %, palladium.

Another subject of the invention is a dehydrogenation catalyst for the conversion of methylpiperidine to methylpyridine, obtainable by a process of the invention. The catalyst of the invention is a solid catalyst. The catalyst comprises a silicon/aluminium core and is covered with an outer layer comprising palladium.

Subject of the invention is also a process for the production of methylpyridine from methylpiperidine, wherein methylpiperidine is contacted with a dehydrogenation catalyst of the invention.

Methylpyridine is also referred to as picoline. The methylpyridine of the invention can either be 2-, 3- or 4-methylpyridine. In line with this, the corresponding methylpiperidine can be 2-, 3- or 4-methylpiperidine. In a preferred embodiment of the invention, the methylpiperidine is 3-methylpiperidine. In this embodiment, 3-methylpiperidine is dehydrogenated to obtain 3-methylpyridine.

In a preferred embodiment of the invention, the reaction is carried out under a hydrogen and/or nitrogen atmosphere.

In a preferred embodiment of the invention, the reaction is carried out in the gaseous phase at a temperature between 180° C. and 400° C., more preferably between 200° C. and 350° C. or 200° C. and 300° C. At these temperatures, the educt and the product are gaseous. Of course, the catalyst remains in a solid state. It is preferred that the methylpiperidine is passed through a reaction zone, in which it is contacted with the catalyst. For example, the catalyst is in a container with an inlet and an outlet, such that the methylpiperidine is fed into the inlet and the product is removed through the outlet. Preferably, the container is a tube, a tube bundle, a pipe or a vessel.

In a preferred embodiment of the invention, the catalyst is mixed with aluminium. Surprisingly, it was found that the catalyst of the invention is so highly reactive that it can be "diluted" with aluminium whilst preserving a high catalytic efficiency. The addition of aluminium is advantageous, because a palladium-based catalyst is expensive and thus the costs can be reduced significantly. For instance, the catalyst can be admixed with 1 to 90 weight %, preferably with 10 to 80 weight % aluminium. It was found that the catalyst is still highly active when two thirds of aluminium granulate are added. It was found that the activity can be further increased when the aluminium is defatted prior to use. The reaction from methylpiperidine to picoline is endothermic, which means that thermal energy has to be supplied to the reaction zone. The addition of aluminium is advantageous, because the aluminium supports the heat transport to the strongly endothermic reaction.

In a preferred embodiment of the invention, the methylpiperidine is initially contacted with a first catalyst/aluminium mixture, and subsequently contacted with a second catalyst/aluminium mixture, wherein the ratio of catalyst/aluminium in the first mixture is lower than in the second mixture. This means, that initially the educt is brought into contact with a reaction zone having a relatively high aluminium content, whereas subsequently the reaction mixture, which already comprises the product at least in part, is brought into contact with a reaction zone having a relatively low aluminium content. It was found that it is advantageous when in the inventive process the methylpiperidine is first contacted with a catalyst mixture with a high aluminium content. Thereby, the good heat transfer properties of the aluminium are exploited. When emerging deeper into the reaction zone, the turnover is decreasing since the amount of educt is decreasing. At this stage, it is advantageous to use a catalyst mixture with a relatively high palladium content. In one embodiment, a catalyst with an increasing gradient of palladium/aluminium can be used in the reaction. In another embodiment, two or more reaction zones comprising mixtures of catalyst with aluminium at different ratios can be employed.

In a preferred embodiment of the invention, the methylpiperidine is produced in a cyclization reaction from methyl-1,5-diaminopentane before the dehydrogenation reaction. The cyclization reaction is carried out in a first reactor and the dehydrogenation reaction is carried out in a second reactor. Both reactors are interconnected and both reactions are carried out in a continuous process. In such an embodiment, the conversion of methyl-1,5-diaminopentane to 3-methylpyridine can be carried out in one continuous process. Such continuous processes are known in the art and for instance disclosed in WO 94/22824 and EP 0 770 687 B1.

In one embodiment, the cyclization catalyst is supplied directly on top of the dehydrogenation catalyst and the methyl-1,5-diaminopentane is supplied from above. However, it is preferred that both catalysts are provided in distinct reactors, which are connected. In this arrangement, the temperatures and the catalysts can be controlled independently. In this embodiment, additional means, such as a condenser or distiller, may be positioned between the two reactors for removing organic substances which have high boiling points. Otherwise, such substances might impact activity and lifetime of the dehydrogenation catalyst.

The methylpiperidine produced in the cyclization reaction is obtained in a mixture with ammonia. In the cyclization reaction, one equivalent ammonia is obtained for each equivalent methylpiperidine. In a preferred embodiment of the invention, the mixture is fed into the second reactor without prior separation of the ammonia. This is advantageous because no removal of ammonia is necessary and the process is considerably simplified.

After the dehydrogenation reaction, the product may be isolated. Alternatively, the product may be directly introduced into a third reactor and subjected to a subsequent synthesis step. The remaining gaseous mixture, optionally after washing out the ammonia, comprises Hydrogen. It may be mixed with air and burned, and the energy thus gained may be retransferred into the process. In an embodiment of the invention, after separation of the product and at least other high molecular weight components and side products, a remaining gaseous mixture is reintroduced into the first reactor.

In a specific embodiment, the reactions are carried out in a nitrogen, hydrogen and ammonia atmosphere. It is preferred that no air or oxygen is added or present, except low impurities. For instance, the gaseous atmosphere comprises more than 50 vol. %, more than 70 vol. % or more than 90 vol. % hydrogen. High levels of hydrogen of above 90 vol. % are applied if an ammonia washer is used in the process. Otherwise, lower levels of about 70 vol. % hydrogen are preferred.

It was found that the inventive catalysts are highly efficient in the conversion of methylpiperidine to methylpyridine. On the one hand, a high yield of methylpyridine is obtained. Preferably, the yield of methylpyridine is above 90, 95 or 97%. In addition, the catalyst was found to be highly stable. It was found that the catalyst can be used at least 300 days when used at temperatures between 285 and 310° C. The lifetime of the catalyst depends on the throughput, and can be enhanced if the throughput is reduced. At lower throughputs, the catalysts could be used for more than 580 days. Normally, the catalyst can be used for at least one year, provided that no air enters the process and no catalyst poisons are present. The high efficiency of the catalyst is obtained as a result of the inventive production method with the specific drying, calcinating and activating steps. The catalyst is also highly efficient, if ammonia is present in the reaction process in high amounts. Due to the high activity, the catalyst can be admixed with aluminium, which saves costs and supports the endothermic reaction.

EXAMPLES

1. Production of a Dehydrogenation Catalyst

A tubular reactor (3 m long, 25 cm diameter) is filled with 75 kg carrier (particles of silica and alumina, Davicat E501™ from Grace Inc.) and ammonia gas (5 kg) is passed above the solid catalyst at room temperature, leading to a neutralisation of acidic surface parts of the carrier and its warm-up to about 60° C. At the same time, a palladium solution is prepared by dissolving 9.5 kg $PdCl_2$ and 14 kg ammonia in 1800 l water. After cooling of the carrier and the palladium solution to room temperature, said palladium solution is pumped over the carrier for 16-24 h. Afterwards, the remaining solution is eluted from the reactor and the catalyst is washed twice with water. The catalyst is dried at 40° C. with air, until most of the water is removed from the catalyst. After drying, the catalyst is calcinated with air at about 130° C. for about 8 hours.

It was found that the catalyst thus obtained can be used in the process for the production of 3-methylpyridine from 3-methylpiperidine at least for 300 days at temperatures between 285 and 310° C. The lifetime of the catalyst depends on the throughput, and can be enhanced if the throughput is reduced. At lower throughputs, the catalysts could be used for more than 580 days.

2. 3-Picolin Production with the Catalyst According to the Invention 300 g catalyst was filled into a reactor vessel. The catalyst was activated with a gaseous mixture of 50% hydrogen and 50% nitrogen (volume/volume) having an initial temperature of 50° C., which was increased to 300° C. Subsequently, a gaseous mixture of methylpiperidine, hydrogen and nitrogen having a temperature of 300° C. was passed over the catalyst. With feed stream of 0.9 kg/h methylpiperidine, 0.3 kg/h nitrogen and 3 g/h hydrogen, the following results were obtained (Table 1):

TABLE 1

| Reaction Time [h] | 3-Picolin yield [%] |
| --- | --- |
| 0:21 | 96.69 |
| 1:21 | 97.07 |
| 12:41 | 98.30 |
| 40:41 | 98.49 |
| 77:06 | 98.40 |
| 100:51 | 98.10 |
| 169:11 | 98.55 |
| 194:19 | 98.43 |
| 256:33 | 98.32 |
| 329:14 | 98.43 |
| 407:21 | 98.42 |

TABLE 1-continued

| Reaction Time [h] | 3-Picolin yield [%] |
| --- | --- |
| 449:51 | 98.39 |
| 476:31 | 98.35 |
| 509:56 | 98.42 |

As can be seen, the catalyst according to the invention allows for the production of 3-picolin with a high yield which remains constant over long periods of time.

The invention claimed is:

1. A process for the production of a catalyst for the dehydrogenation of methylpiperidine to methylpyridine comprising in the order (a) to (d) the step of
   (a) providing a carrier comprising 65-100 weight % silicon oxide and 0-35 weight % aluminium oxide,
   (b) impregnating the carrier with palladium, whereby the carrier is brought into contact with an aqueous solution of a palladium-ammonia-complex to obtain a catalyst,
   (c) drying the catalyst with air at a temperature between 20-60° C. and
   (d) calcinating the catalyst at a temperature between 80-200° C.

2. The process of claim 1, further comprising after step (d)
   (e) activating the catalyst with hydrogen.

3. The process of claim 2, wherein the activating step (c) is carried out under active depletion of oxygen.

4. The process of claim 1, wherein the catalyst comprises 0.5 to 8 weight % palladium.

5. A dehydrogenation catalyst for the conversion of methylpiperidine to methylpyridine, obtainable by a process of claim 1, which can be used is said process for at least 300 days when used at temperatures between 285-310° C.

* * * * *